United States Patent
Wang et al.

(10) Patent No.: US 11,801,083 B2
(45) Date of Patent: Oct. 31, 2023

(54) METHOD AND APPARATUS FOR ADJUSTING IN-TANK PRESSURE OF WORKING MEDIUM STORAGE TANK

(71) Applicant: HYGEA MEDICAL TECHNOLOGY CO., LTD., Beijing (CN)

(72) Inventors: Shi Wang, Beijing (CN); Fei Xiong, Beijing (CN); Jian Xiao, Beijing (CN); Qianfu Huang, Beijing (CN)

(73) Assignee: HYGEA MEDICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 18/008,474

(22) PCT Filed: May 27, 2022

(86) PCT No.: PCT/CN2022/095531
§ 371 (c)(1),
(2) Date: Dec. 6, 2022

(87) PCT Pub. No.: WO2023/273736
PCT Pub. Date: Jan. 5, 2023

(65) Prior Publication Data
US 2023/0190354 A1    Jun. 22, 2023

(30) Foreign Application Priority Data

Jun. 30, 2021 (CN) .......................... 202110741786.2

(51) Int. Cl.
*A61B 18/02* (2006.01)
*A61B 18/04* (2006.01)
*A61B 18/00* (2006.01)

(52) U.S. Cl.
CPC .... *A61B 18/02* (2013.01); *A61B 2018/00041* (2013.01); *A61B 2018/00577* (2013.01);
(Continued)

(58) Field of Classification Search
CPC .......... A61B 18/02; A61B 2018/00041; A61B 2018/00577; A61B 2018/00642;
(Continued)

(56) References Cited

U.S. PATENT DOCUMENTS

| 5,800,488 A * | 9/1998 | Crockett ................ A61B 18/02 607/105 |
| 2002/0068929 A1* | 6/2002 | Zvuloni ................ A61B 18/02 606/22 |

(Continued)

FOREIGN PATENT DOCUMENTS

| CN | 101706328 A | 5/2010 |
| CN | 105822386 A | 8/2016 |

(Continued)

OTHER PUBLICATIONS

1st Office Action of counterpart Chinese Patent Application No. 202110741786.2 dated May 7, 2022.

(Continued)

*Primary Examiner* — Daniel W Fowler

(57) ABSTRACT

Provided are a method for adjusting an in-tank pressure of a working medium storage tank and an apparatus for the same. The method includes: acquiring a backflow temperature collected by each of first thermocouples; counting the number of target backflow paths whose backflow temperature reaches a preset temperature; and adjusting an in-tank pressure of the working medium storage tank to a target in-tank pressure corresponding to the number of the target backflow paths according to the number of the target backflow paths and a corresponding relationship between a preset number of backflow paths and the in-tank pressure. The control box determines the target in-tank pressure corresponding to the number of the target backflow paths to (Continued)

realize automatic adjustment of the in-tank pressure of the working medium storage tank.

12 Claims, 14 Drawing Sheets

(52) U.S. Cl.
CPC ............... *A61B 2018/00642* (2013.01); *A61B 2018/00696* (2013.01); *A61B 2018/00815* (2013.01); *A61B 2018/00821* (2013.01); *A61B 2018/0212* (2013.01); *A61B 2018/0268* (2013.01)

(58) Field of Classification Search
CPC ........... A61B 2018/00696; A61B 2018/00815; A61B 2018/00821; A61B 2018/0212; A61B 2018/0268
See application file for complete search history.

(56) References Cited

U.S. PATENT DOCUMENTS

| | | | |
|---|---|---|---|
| 2007/0244474 A1* | 10/2007 | DeLonzor | A61B 18/02 606/23 |
| 2008/0132976 A1 | 6/2008 | Kane et al. | |
| 2009/0163902 A1* | 6/2009 | DeLonzor | A61B 18/02 606/22 |
| 2009/0299357 A1* | 12/2009 | Zhou | A61B 18/02 606/21 |
| 2009/0306638 A1* | 12/2009 | Hillely | A61B 5/01 600/549 |
| 2014/0228831 A1* | 8/2014 | Fischer | A61B 18/02 606/20 |
| 2017/0000543 A1 | 1/2017 | Mahrouche et al. | |
| 2019/0328437 A1* | 10/2019 | Perron | A61B 18/02 |

FOREIGN PATENT DOCUMENTS

| | | |
|---|---|---|
| CN | 107951559 A | 4/2018 |
| CN | 210019629 U | 2/2020 |
| CN | 110953779 A | 4/2020 |
| CN | 212879546 U | 4/2021 |

OTHER PUBLICATIONS

Notice of Allowance of counterpart Chinese Patent Application No. 202110741786.2 dated May 31, 2022.

* cited by examiner

METHOD AND APPARATUS FOR ADJUSTING IN-TANK PRESSURE OF WORKING MEDIUM STORAGE TANK

CROSS-REFERENCE TO RELATED APPLICATIONS

This application claims the priority of Chinese patent application CN 202110741786.2, entitled "Method and Apparatus for Adjusting In-tank Pressure of Working Medium Storage Tank" and filed on Jun. 30, 2021, the entirety of which is incorporated herein by reference.

FIELD OF THE INVENTION

The disclosure relates to the technical field of medical instruments, and in particular, to a method for adjusting an in-tank pressure of a working medium storage tank. The disclosure also relates to an apparatus for adjusting an in-tank pressure of a working medium storage tank, a control box, a computer readable storage medium, and a combined cryoablation and hyperthermia system.

BACKGROUND OF THE INVENTION

A combined cryoablation and hyperthermia system is a minimally invasive device for treating a tumor using a physical therapy. As shown by clinical data, a single cryogenic therapy or thermal therapy may have a killing effect on tumor tissues. However, if cryogenic therapy is not performed thoroughly, cancer cell tissues may not be destroyed completely, a pain in the human body is slightly strong, and a high temperature may stimulate blood circulation, which may facilitate spreading of the cancer cells along a blood vessel. Therefore, a composite tumor treatment device which combines the deep cryogenic therapy and the thermal therapy can play a better role in the cancer treatment field.

During a surgery, a surgeon clicks a cryogenic discharging button or a thermal discharging button, and opens a working medium discharging valve, so that the working medium is delivered to an ablation probe via a delivery pipe. Then, the surgeon operates the ablation probe to kill the cancer cells. As the temperature of the tumor tissues reaches a treatment temperature, the same working medium flow will go beyond the amount required for maintaining the treatment temperature, and this process easily leads to a waste of the working medium.

SUMMARY OF THE INVENTION

In view of this, an embodiment of the disclosure provides a method for adjusting an in-tank pressure of a working medium storage tank. The disclosure also relates to an apparatus for adjusting an in-tank pressure of a working medium storage tank, a control box, a computer readable storage medium, and a combined cryoablation and hyperthermia system, so as to solve technical defects in existing technologies.

According a first aspect of embodiments of the disclosure, a method for adjusting an in-tank pressure of a working medium storage tank is provided. The method is applied to a control box of a combined cryoablation and hyperthermia system; the combined cryoablation and hyperthermia system includes the control box, a working medium storage tank for storing a working medium, a valve box provided with multiple working medium discharging valves, a working medium delivery pipe connected to an outlet of each of the multiple working medium discharging valves and for delivering the working medium to an ablation probe, and a first thermocouple provided in each of working medium delivery pipes and for collecting a backflow temperature of each of paths; and the method for adjusting the in-tank pressure of the working medium storage tank includes steps of:
acquiring a backflow temperature collected by each of first thermocouples;
counting the number of target backflow paths whose backflow temperature reaches a preset temperature; and
adjusting an in-tank pressure of the working medium storage tank to a target in-tank pressure corresponding to the number of the target backflow paths according to the number of the target backflow paths and a corresponding relationship between a preset number of backflow paths and the in-tank pressure.

Optionally, the working medium storage tank includes a cold tank for storing a cold working medium; and
the step of counting the number of target backflow paths whose backflow temperature reaches the preset temperature includes a step of:
counting the number of target backflow paths whose backflow temperature is not higher than a first preset temperature.

Optionally, the step of adjusting the in-tank pressure of the working medium storage tank to the target in-tank pressure corresponding to the number of the target backflow paths according to the number of the target backflow paths and a corresponding relationship between the preset number of the backflow paths and the in-tank pressure includes steps of:
determining a target in-tank pressure corresponding to the number of the target backflow paths according to the number of the target backflow paths and the corresponding relationship between the preset number of the backflow paths and the in-tank pressure; and
sending an adjustment instruction carrying the target in-tank pressure to the cold tank, the adjustment instruction instructing the cold tank to open a pressurization valve or an air escape valve so as to adjust the in-tank pressure of the cold tank to the target in-tank pressure.

Optionally, a phase separation valve is further provided in the valve box; and
before the step of acquiring the backflow temperature collected by each of first thermocouples, the method further includes steps of:
detecting an opened-closed state of each of cold valves, the cold valve being a discharging valve of the cold working medium;
counting the number of cold valves in an opened state;
sending an opening instruction to the valve box if the number is not greater than a preset number, the opening instruction instructing opening of the phase separation valve; and
sending a closing instruction to the valve box if the number is greater than the preset number, the closing instruction instructing closing of the phase separation valve.

Optionally, a second thermocouple is provided at the phase separation valve; and
after the step of sending the opening instruction to the valve box, the method further includes steps of:
acquiring a temperature at the phase separation valve collected by the second thermocouple; and sending a closing instruction to the valve box if the temperature at the phase separation valve is not higher than a second preset temperature.

Optionally, the working medium storage tank includes a hot tank for storing a hot working medium; and
the step of counting the number of target backflow paths whose backflow temperature reaches the preset temperature includes a step of:
counting the number of target backflow paths whose backflow temperature is not lower than a third preset temperature.

Optionally, the step of adjusting the in-tank pressure of the working medium storage tank to the target in-tank pressure corresponding to the number of the target backflow paths according to the number of the target backflow paths and a corresponding relationship between the preset number of the backflow paths and the in-tank pressure includes steps of:
determining a target in-tank pressure corresponding to the number of the target backflow paths according to the number of the target backflow paths and the corresponding relationship between the preset number of backflow paths and the in-tank pressure; and
sending an adjustment instruction carrying the target in-tank pressure to the hot tank, the adjustment instruction instructing the hot tank to turn on a heater or open an air escape valve so as to adjust the in-tank pressure of the hot tank to the target in-tank pressure.

Optionally, the control box is provided therein with a temperature collecting circuit board and with a fan and a heater for adjusting an ambient temperature of the temperature collecting circuit board; and a temperature sensor is provided on the temperature collecting circuit board; and
the method further includes steps of:
acquiring an ambient temperature collected by the temperature sensor;
actuating the heater to work if the ambient temperature is lower than a fourth preset temperature; and
actuating the fan to work if the ambient temperature is higher than a fifth preset temperature, the fifth preset temperature being higher than the fourth preset temperature.

Optionally, the heater is connected to a normally open contact of a first relay, and a positive temperature coefficient thermistor is connected in series in a coil loop of the first relay; and
the step of actuating the heater to work if the ambient temperature is lower than the fourth preset temperature includes a step of:
actuating the heater to work with the normally open contact of the first relay closed if the ambient temperature is lower than the fourth preset temperature, a resistance value of the positive temperature coefficient thermistor is decreased to a first preset resistance value, and a current passing through the coil loop of the first relay is increased to a first preset current value.

Optionally, the fan is connected to a normally open contact of a second relay, and a negative temperature coefficient thermistor is connected in series in a coil loop of the second relay; and
the step of actuating the fan to work if the ambient temperature is higher than the fifth preset temperature includes a step of:
actuating the fan to work with the normally open contact of the second relay closed if the ambient temperature is higher than the fifth preset temperature, a resistance value of the negative temperature coefficient thermistor is decreased to a second preset resistance value, and a current passing through the coil loop of the second relay is increased to a second preset current value.

According to a second aspect of embodiments of the disclosure, it provides an apparatus for adjusting an in-tank pressure of a working medium storage tank. The apparatus includes:
a backflow temperature acquiring module, which is configured to acquire a backflow temperature collected by each of first thermocouples;
a target backflow path counting module, which is configured to count the number of target backflow paths whose backflow temperature reaches a preset temperature; and
a pressure adjusting module, which is configured to adjust an in-tank pressure of the working medium storage tank to a target in-tank pressure corresponding to the number of the target backflow paths according to the number of the target backflow paths and a corresponding relationship between a preset number of backflow paths and the in-tank pressure.

According to a third aspect of embodiments of the disclosure, it provides a control box. The control box includes:
a memory and a processor; and
the memory is configured to store a computer executable instruction, and the processor is configured to execute the computer executable instruction, so as to implement steps of the method provided according to the first aspect of embodiments of the disclosure.

According to a fourth aspect of embodiments of the disclosure, it provides a computer readable storage medium. The computer readable storage medium stores a computer executable instruction, and the computer executable instruction, when executed by a computer, implements steps of the method provided according to the first aspect of embodiments of the disclosure.

According to a fifth aspect of embodiments of the disclosure, it provides a combined cryoablation and hyperthermia system. The combined cryoablation and hyperthermia system includes the control box provided according to the third aspect of embodiments of the disclosure, a working medium storage tank for storing a working medium, a valve box provided with multiple working medium discharging valves, a working medium delivery pipe connected to an outlet of each of the multiple working medium discharging valves and for delivering the working medium to an ablation probe, and a first thermocouple provided in each of working medium delivery pipes and for collecting a backflow temperature of each of paths.

Optionally, a base includes a fixation base having a hollow cavity, and a tube fixed in the hollow cavity of the fixation base. A temperature probe lead is sealed in the tube, and a temperature measuring end passes through tube and exposes to the outside. A distance between an end portion of the temperature measuring end to an end portion of the tube does not exceed 2 mm.

Optionally, the end portion of the tube passes through the hollow cavity of the fixation base, and a distance from the end portion of the tube to an end portion of the fixation base is at least 3 mm.

Optionally, temperature probe lead and the tube are sealed together by a cure adhesive, and the cure adhesive is obtained by mixing glue and a coagulator according to a preset ratio.

In the embodiments of the disclosure, the combined cryoablation and hyperthermia system includes the control box, the working medium storage tank for storing the working medium, the valve box provided with multiple working medium discharging valves, the working medium delivery pipe connected to the outlet of each of the multiple working medium discharging valves and for delivering the working medium to the ablation probe, and the first thermocouple provided in each of the working medium delivery pipes and for collecting the backflow temperature of each of paths. The control box acquires the backflow temperature collected by each of the first thermocouples, counts the number of the target backflow paths whose backflow temperature reaches the preset temperature, and adjusts the in-tank pressure of the working medium storage tank to the target in-tank pressure corresponding to the number of the target backflow paths according to the number of the target backflow paths and the corresponding relationship between the preset number of the backflow paths and the in-tank pressure.

The control box determines the target in-tank pressure corresponding to the number of the target backflow paths to realize automatic adjustment of the in-tank pressure of the working medium storage tank by acquiring the backflow temperature collected by each of the first thermocouples and counting the number of the target backflow paths whose backflow temperature reaches the preset temperature, and makes the flow of the working medium delivered change automatically accordingly to better adapt to an actual treatment scene and reduce the unnecessary waste of the working medium by automatically adjusting the in-tank pressure of the working medium storage tank.

DETAILED DESCRIPTION OF THE EMBODIMENTS

Many specific details are described in the following description for better understanding the disclosure. However, the disclosure may be implemented in other ways different from those described herein, and those skilled in the art can make similar generalizations without departing from the spirit of the disclosure. Therefore, the disclosure is not limited by the following specific embodiments disclosed.

Terms used in one or more embodiments of the disclosure are for the purpose of describing specific embodiments only, rather than limiting one or more embodiments of the disclosure. The singular form, such as "a", "the", and "this" used in one or more embodiments and claims of the disclosure also intends to include the plural form, unless other meanings are indicated expressly in the context. It should also be understood that, the wording of "and/or" used in one or more embodiments of the disclosure refers to and includes any possible combination or all possible combinations of one or more associated listed items.

It should be understood that, although wordings, such as first and second, may be used to describe various kinds of information in one or more embodiments of the disclosure, the information shall not be limited to these wordings. These wordings are only used to distinguish the same kind of information from each other. For example, without departing from the scope of one or more embodiments of the disclosure, a first may be called a second, and similarly the second may be called the first. Depending on the context, for example, the word "if" used herein may be explained as "during", "when", or "in response to a determination".

It provides a method for adjusting an in-tank pressure of a working medium storage tank in the disclosure. The disclosure also relates to an apparatus for adjusting an in-tank pressure of a working medium storage tank, a control box, a computer readable storage medium, and a combined cryoablation and hyperthermia system, which will be described in the following embodiments one by one in detail.

Figure 1:
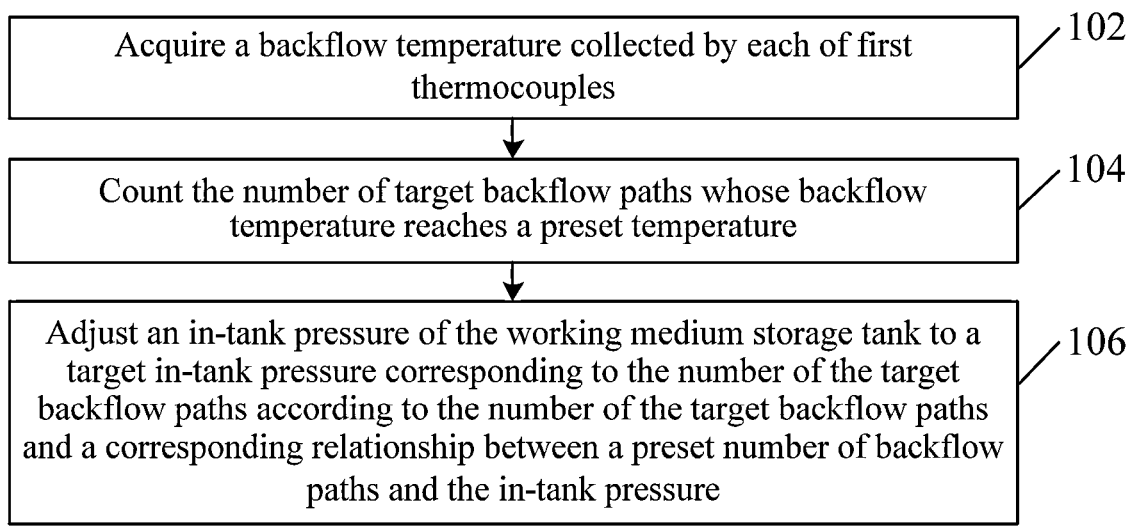
FIG. 1 schematically shows a flowchart of a method for adjusting an in-tank pressure of a working medium storage tank provided according to an embodiment of the disclosure.

FIG. 1 schematically shows a flowchart of a method for adjusting an in-tank pressure of a working medium storage tank provided according to an embodiment of the disclosure, and this method is applied to a control box in a combined cryoablation and hyperthermia system. The combined cryoablation and hyperthermia system includes the control box, a working medium storage tank for storing a working medium, a valve box provided with multiple working medium discharging valves, a working medium delivery pipe connected to an outlet of each of the multiple working medium discharging valves and for delivering the working medium to an ablation probe, and a first thermocouple provided in each of working medium delivery pipes and for collecting a backflow temperature of each of paths. This method specifically includes the following steps.

At step 102, a backflow temperature collected by each of first thermocouples is acquired.

A first thermocouple is provided in each of the working medium delivery pipes. The first thermocouple is configured to collect the backflow temperature in the working medium delivery pipe and send the backflow temperature collected to the control box. A temperature collecting circuit board is provided in the control box. The temperature collecting circuit board may realize a conversion between a physical signal and an electrical signal of a temperature value and realize a communication function.

Figure 2:
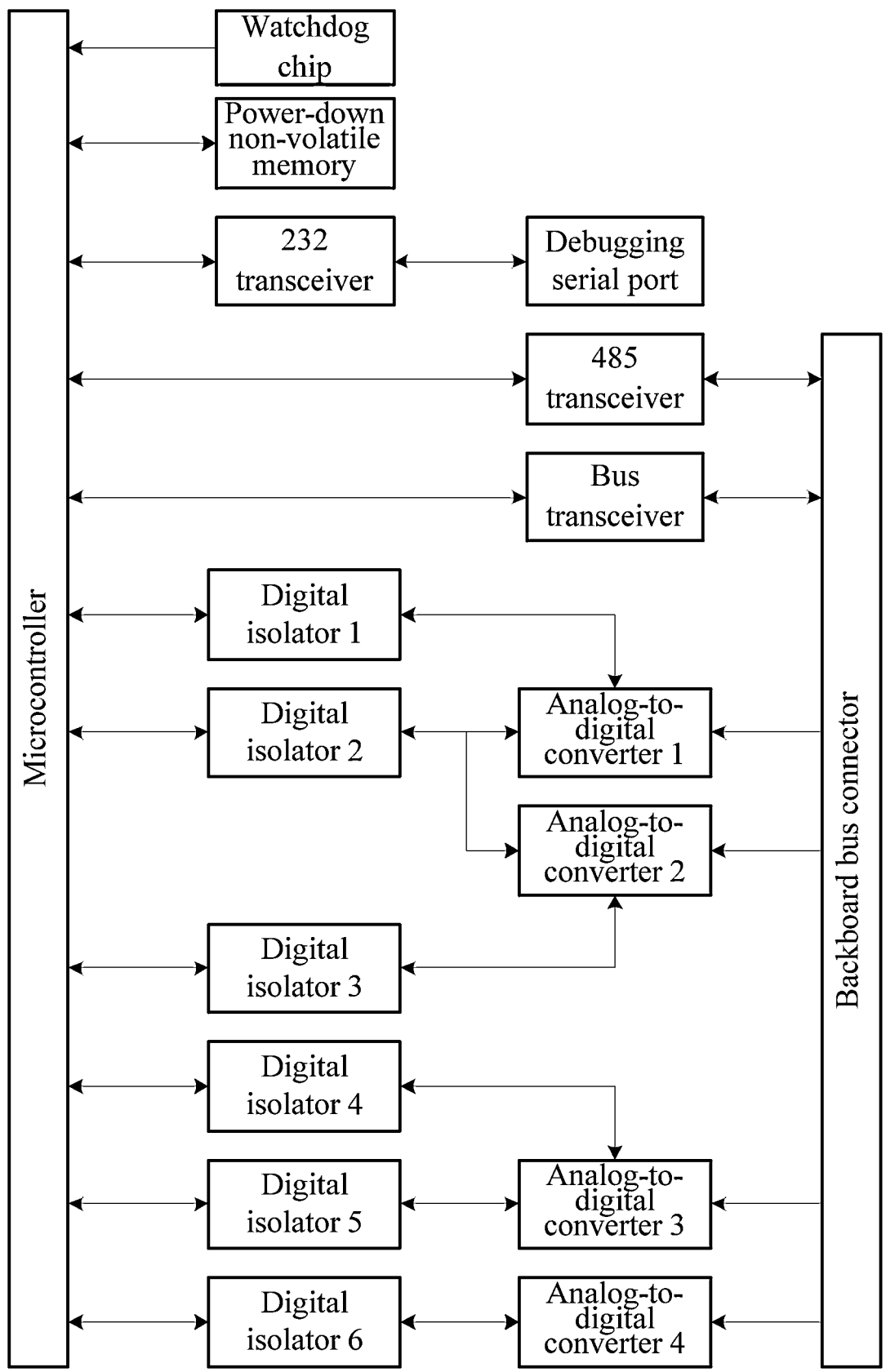
FIG. 2 schematically shows a hardware structure of a temperature collecting circuit provided according to an embodiment of the disclosure.

In an embodiment of the disclosure, a structure of the temperature collecting circuit board is as shown in FIG. 2. The temperature collecting circuit board mainly has the following functions. Analog-to-digital converters 1, 2, and 3 realize a temperature collecting function of 12 thermocouples, and a temperature collecting range is from −200° C. to 100° C. with a precision error less than 3° C. An analog-to-digital converter 4 realizes 2 channels temperature collecting function of temperature sensors on the board, which is used as temperature compensation for the 12 thermocouples. A bus transceiver realizes one bus, communicates with a main control board, and is configured to send the backflow temperature collected to the main control board, so that the main control board performs a corresponding pressure adjustment based on the backflow temperature. Herein, the bus may be a CAN bus. An indicator light on the board is configured to indicate an operation state of the temperature collecting circuit board. If the temperature collecting circuit board operates normally, the indicator light may be green, and if the temperature collecting circuit board is abnormal, the indicator light may be red. A power-down non-volatile memory is configured to realize a parameter storage function. A watchdog chip is configured to prevent a program running deviation, and has an address identification function for realizing a unique identification of an inserted board. A 485 transceiver is configured to realize a 485 communication function and to realize firmware upgrade of the inserted board.

When collecting data of the thermocouple, the analog-to-digital converters 1, 2, and 3 use an external reference voltage of 2.048 V. A collectable temperature range of the thermocouple is from −200° C. to 100° C., and a corresponding collectable signal range at a signal input end of the analog-to-digital converter is from −5.603 mV to 4.279 mV. An ADS1248 chip may be selected as the analog-to-digital converter, and has a maximum gain of 128. Therefore, a value of the maximum gain of the analog-to-digital converters 1, 2, and 3 is set as 128.

When collecting data of the temperature sensor, an excitation current is 250 uA, and a sampling resistance is 3.24 kΩ, the analog-to-digital converter 4 using an external reference voltage of 1.62 V. A collectable temperature range of the temperature sensor is from −200° C. to 100° C., and correspondingly a resistance range of the temperature sensor is from 20Ω to 140Ω. An ADS1248 chip may be selected as the analog-to-digital converter, and a corresponding range of a signal to be collected is from 5 mV to 35 mV. Therefore, a value of a maximum gain of the analog-to-digital converter 4 is set as 32. A PT100 may be selected as the temperature sensor.

The ADS1248 chip supports a maximum sampling rate of 2000SPS. In actual application, the temperature to be collected does not change transiently, and thus the sampling rate of the ADS1248 chip is set as 160 SPS.

Figure 3A:
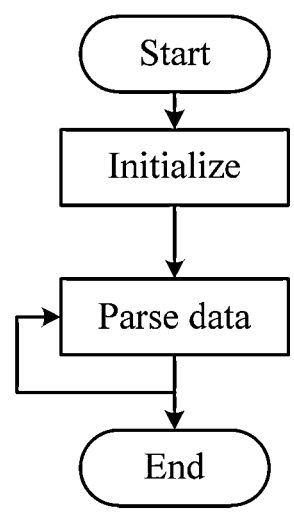
FIG. 3a schematically shows a flowchart of temperature collecting provided according to an embodiment of the disclosure.
Figure 3B:
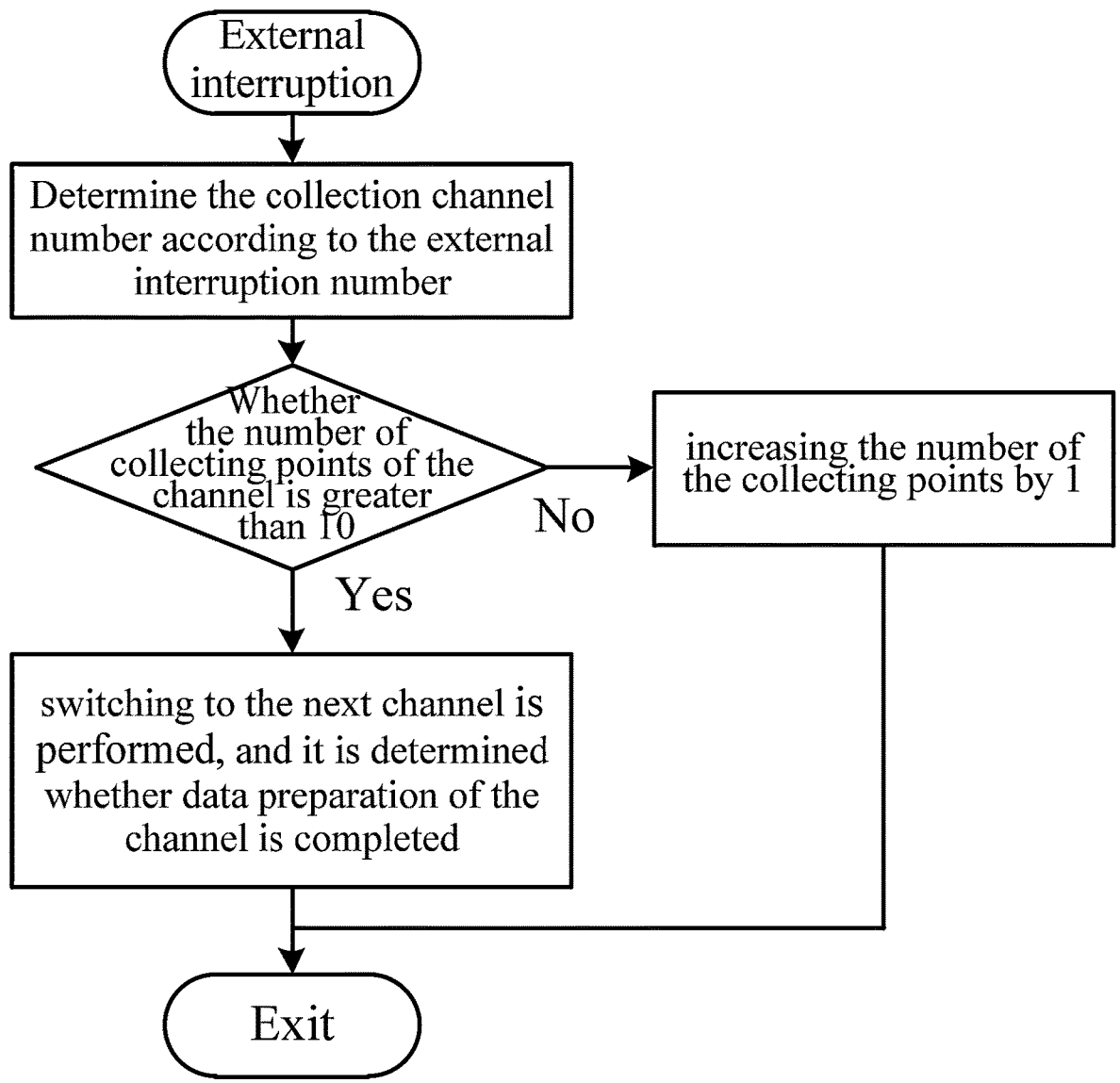
FIG. 3b schematically shows a flowchart of external interruption provided according to an embodiment of the disclosure.
Figure 3C:
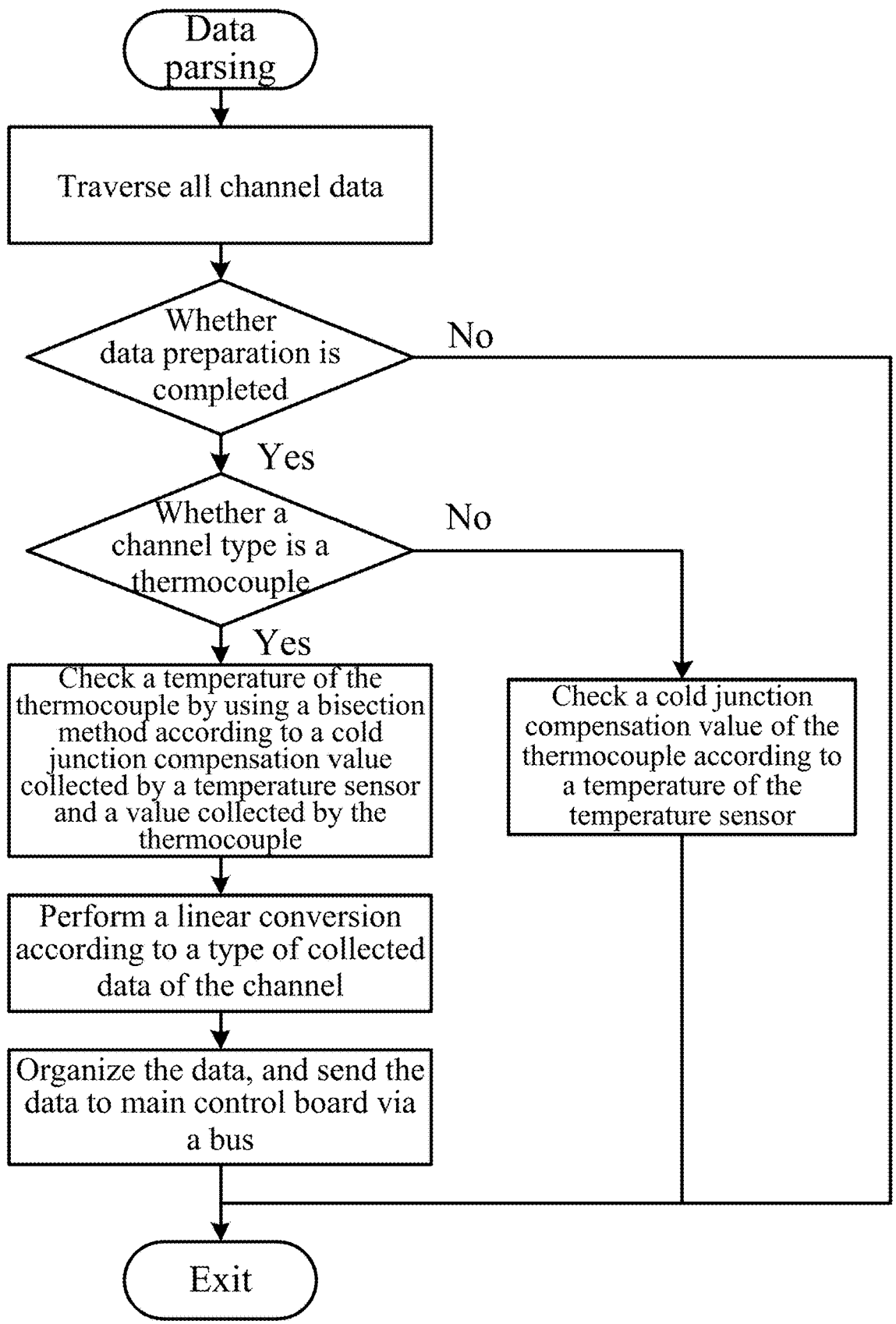
FIG. 3c schematically shows a flowchart of data parsing provided according to an embodiment of the disclosure.

In an embodiment of the disclosure, a flow of temperature collecting is as shown in FIG. 3a, and mainly includes two steps, i.e., initializing and parsing data. Initializing involves a process of external interruption. The process of the external interruption is as shown in FIG. 3b, and mainly includes the following steps. The collection channel number is determined according to the external interruption number; it is determined whether the number of collecting points of this channel is greater than 10; if the number of the collecting points is greater than 10, switching to the next channel is performed, and it is determined that data preparation of the channel is completed; and if the number of the collecting points is not greater than 10, the number of the collecting points is increased by 1 to continue data collecting. A process of data parsing is as shown in FIG. 3c, and mainly includes the following steps. All channel data is traversed; it is determined whether data preparation is completed; and if the data preparation is completed, it is determined whether a channel type is a thermocouple; if the channel type is the thermocouple, a temperature of the thermocouple is checked by using a bisection method according to a cold junction compensation value collected by the temperature sensor and a value collected by the thermocouple; a linear conversion is performed according to a type of collected data of the channel; the data is organized, and is sent to the main control board via the bus; and if the channel type is not the thermocouple, a cold junction compensation value of the thermocouple is checked according to a temperature of the temperature sensor.

At present, a deep hypothermia and hyperthermia play a crucial role in the surgery, and the surgeon needs to adjust a therapeutic schedule in real time based on the backflow temperature. Therefore, it is necessary to show the backflow temperature quickly and accurately. In an embodiment of the disclosure, the combined cryoablation and hyperthermia system further includes an upper computer. After step 102, the method further includes: sending a backflow temperature collected by each of the first thermocouples to the upper computer for display.

Figure 4:
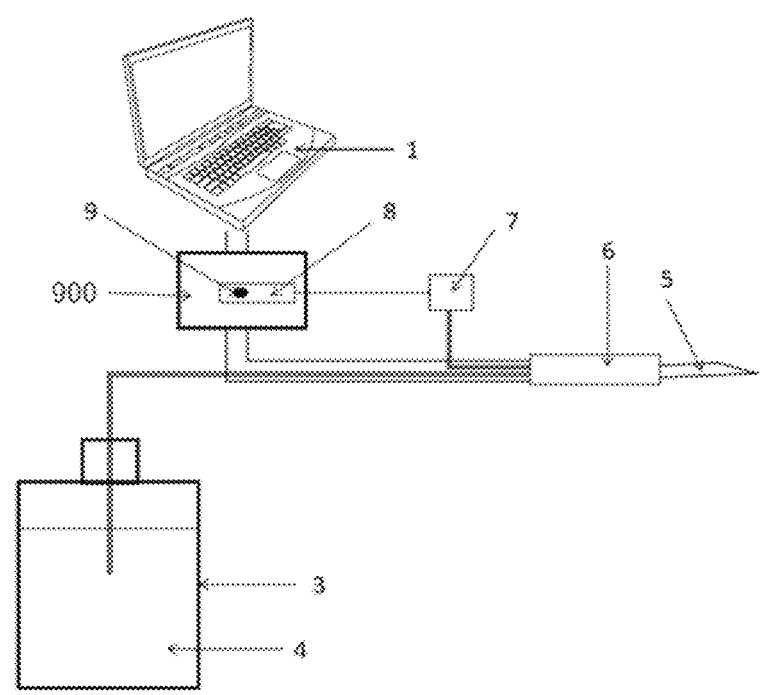
FIG. 4 schematically shows a structure of a combined cryoablation and hyperthermia system provided according to an embodiment of the disclosure.

The combined cryoablation and hyperthermia system is as shown in FIG. 4. The system includes an upper computer 1, a control box 900, a working medium storage tank 3, an ablation probe 5, a working medium delivery pipe 6, and a first thermocouple 7. The control box 900 communicates with the upper computer 1, and delivers a working medium 4 from the inside of the working medium storage tank 3 to the inside of the working medium delivery pipe 6, and reach a tip portion of the ablation probe 5 for performing a treatment. Then, a backflow temperature is collected by the first thermocouple 7, and a temperature value is displayed on an interface of the upper computer 1 for providing references to the surgeon. The temperature value is recorded in real time, and a temperature curve is plotted, so as to provide convenience for the surgeon to adjust the therapeutic schedule.

In a temperature measurement solution of a common thermocouple, there is cold junction compensation. If a position of the cold junction compensation is not appropriate, the thermocouple may easily be affected by an ambient temperature, which causes temperature drift. A temperature measurement principle of the common thermocouple is as follows. A certain thermoelectric potential corresponds to a certain temperature value, and a corresponding relationship of the two can be found in a thermocouple indexing table. However, temperatures at reference ends are all 0° C., but in actual application, it is neither possible nor convenient to maintain an on-site temperature at 0° C. Therefore, the cold junction compensation is necessary in the temperature measurement of the thermocouple. That is, a temperature value of the thermocouple is a sum of a temperature value of the cold junction compensation and a temperature value of a subject measured. Therefore, if a compensation temperature is relatively low, a finally displayed temperature value is lower than an actual value, and if the compensation temperature is relatively high, the finally displayed temperature value is higher than the actual value.

In order to handle this problem, in an embodiment of the disclosure, the control box is provided therein with a temperature collecting circuit board and with a fan and a heater for adjusting the ambient temperature of the temperature collecting circuit board; and a temperature sensor is provided on the temperature collecting circuit board. The method may further include the following steps. An ambient temperature collected by the temperature sensor is acquired; if the ambient temperature is lower than a fourth preset temperature, the heater is actuated to work; and if the ambient temperature is higher than a fifth preset temperature, the fan is actuated to work, the fifth preset temperature being higher than the fourth preset temperature.

Figure 5:
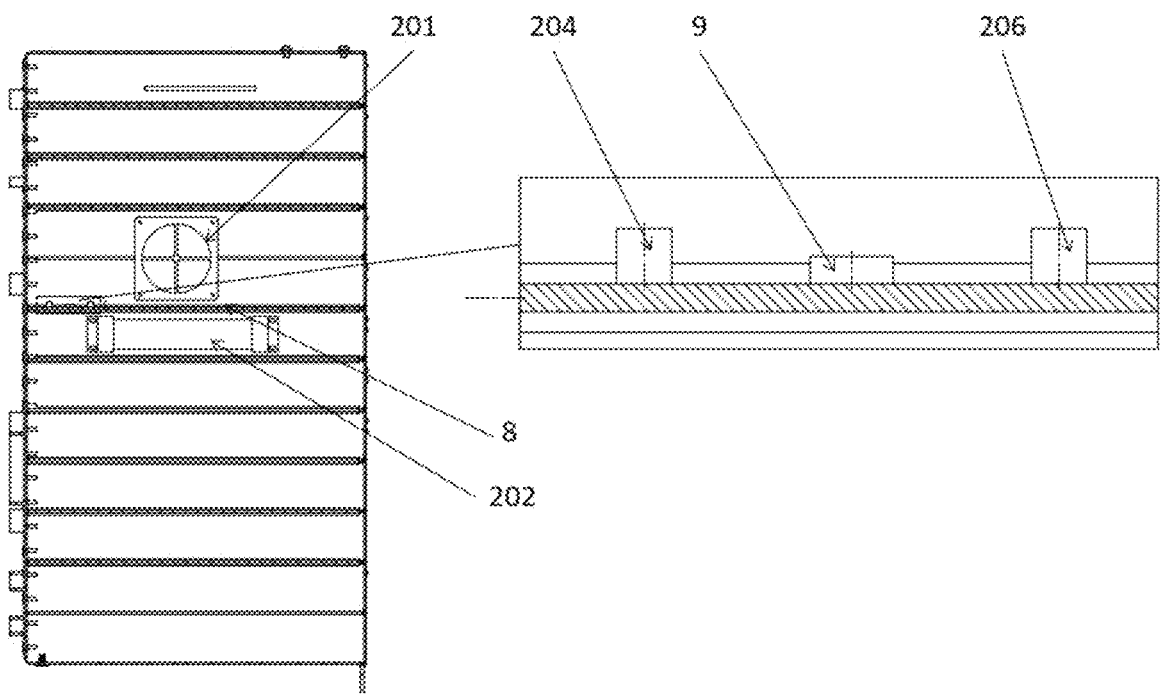
FIG. 5 schematically shows a structure for controlling a cold junction compensation temperature to be constant provided according to an embodiment of the disclosure.

A hardware structure of the temperature collecting circuit board is as shown in FIG. 2, and a PT100 may be selected as the temperature sensor. In the combined cryoablation and hyperthermia system shown in FIG. 4, the thermocouple 7 and a temperature collecting circuit board 8 are connected via a thermocouple cable 12. A cold junction compensation point 9 is located on the temperature collecting circuit board 8. The temperature collecting circuit board 8 is located in the control box 900. The environment where the control box 900 is located is an area where the temperature changes sharply. The lowest temperature may reach −60° C., and the highest temperature may reach 40° C. In order to prevent an influence of the ambient temperature on the cold junction compensation point 9, it provides a constant control structure of a cold junction compensation temperature as shown in FIG. 5. The control box 900 is provided therein with a fan 201 and a heater 202. The cold junction compensation point 9 is prevented from temperature drift due to the influence of the ambient temperature by controlling the fan 201 and the heater 202. Specifically, the ambient temperature collected by the temperature sensor is acquired in real time. If the ambient temperature is too low, for example, lower than 20° C., the heater is actuated to work, so that the ambient temperature increases. If the ambient temperature is too high, for example, higher than 25° C., the fan is actuated to work, so that the ambient temperature decreases. If the ambient temperature is between 20° C. and 25° C., the heater and the fan may be actuated to work at the same time, so that the ambient temperature is maintained between 20° C. and 25° C.

A manner of actuating the heater and the fan to work may be implemented by issuing an instruction, namely that the instruction is issued to the heater/fan by a program control for actuating the heater/fan to work. In another implementation manner, actuating the heater and the fan to work may be implemented by a hardware circuit.

In an embodiment of the disclosure, the heater is connected to a normally open contact of a first relay. A positive temperature coefficient thermistor is connected in series in a coil loop of the first relay. Correspondingly, if the ambient temperature is lower than a fourth preset temperature, a step of actuating the heater to work is specifically implemented through the following steps. If the ambient temperature is lower than the fourth preset temperature, a resistance value of the positive temperature coefficient thermistor is decreased to a first preset resistance value, and a current passing through the coil loop of the first relay is increased to a first preset current value, so that the normally open contact of the first relay is closed to actuate the heater to work.

As shown in FIG. 5, a positive temperature coefficient thermistor 206 (the higher the temperature is, the greater the resistance is, and the lower the temperature is, the smaller the resistance is) is connected in series in a coil loop of the first relay, and a heater 202 is connected to the normally open contact of the first relay. When the ambient temperature is relatively low (lower than the fourth preset temperature), the resistance value of the positive temperature coefficient thermistor 206 is decreased, and the current passing through the coil loop of the relay is increased. When the current is increased to the first preset current value, the normally open contact of the first relay is closed and the heater 202 begins to work. After the heater 202 operates for a while, the temperature increases. The resistance value of the positive temperature coefficient thermistor 206 is increased, and the current passing through the coil loop of the first relay is decreased, so that the normally open contact of the first relay is opened and the heater 202 stops to work.

In an embodiment of the disclosure, the fan is connected to a normally open contact of a second relay. A negative temperature coefficient thermistor is connected in series in a coil loop of the second relay. Correspondingly, if the ambient temperature is higher than a fifth preset temperature, a step of actuating the fan to work is specifically implemented through the following steps. If the ambient temperature is higher than the fifth preset temperature, a resistance value of the negative temperature coefficient thermistor is decreased to a second preset resistance value, and a current passing through the coil loop of the second relay is increased to a second preset current value, so that the normally open contact of the second relay is closed to actuate the fan to work.

As shown in FIG. 5, a negative temperature coefficient thermistor 204 (the higher the temperature is, the smaller the resistance is, and the lower the temperature is, the greater the resistance is) is connected in series in a coil loop of the second relay, and a fan 201 is connected to the normally open contact of the second relay. When the temperature is higher, the resistance value of the negative temperature coefficient thermistor 204 is decreased, and the current passing through the coil loop of the second relay is increased, so that the normally open contact of the second relay is closed and the fan 201 begins to work. After the fan 201 operates for a while, the temperature decreases. The resistance value of the negative temperature coefficient thermistor 206 is increased, and the current passing through the coil loop of the second relay is decreased, so that the normally open contact of the second relay is opened and the fan 201 stops to work.

At step 104, the number of target backflow paths whose backflow temperature reaches a preset temperature is counted.

After the control box (specifically the main control board in the control box) acquires the backflow temperature collected by each of the first thermocouple, the control box may perform a determination on the magnitude of the backflow temperature to determine whether the backflow temperature reaches a preset temperature. The preset temperature refers to a set temperature that can play a role of killing tumor cells. For example, for a cold working medium, when the temperature is below −190° C., the tumor cells may be better frozen and killed after heat exchanging with the tumor cells is performed. Thus, for the cold working medium, the preset temperature is −190° C. For the hot working medium, when the temperature is above 85° C., the tumor cells may be better killed after heat exchanging with the tumor cells is performed. Thus, for the hot working medium, the preset temperature is 85° C.

In an embodiment of the disclosure, one working medium delivery pipe is one backflow path, and one first thermocouple is provided in each of the working medium delivery pipes. Then, after performing a determination on the backflow temperature collected, the number of target backflow paths whose backflow temperature reaches the preset temperature may be counted. The greater the number of the target backflow paths is, it is indicated that multiple ablation probes may reach the preset temperature. When the target backflow paths are combined, it is clear that the temperature exceeds the preset temperature. In order to avoid a waste of the working medium, an in-tank pressure of the working medium storage tank may be reduced properly, to reduce a flow of the working medium discharged, thereby reducing the waste of the working medium.

At step 106, an in-tank pressure of the working medium storage tank is adjusted to a target in-tank pressure corresponding to the number of the target backflow paths according to the number of the target backflow paths and a corresponding relationship between a preset number of backflow paths and the in-tank pressure.

A corresponding relationship between the number of the backflow paths and the in-tank pressure may be stored in advance in a storage medium of the control box. This corresponding relationship is generally set according to experience, in order to maximize the utilization rate of the working medium. After the number of the target backflow paths is counted, the target in-tank pressure corresponding to the number of the target backflow paths is determined according to a preset corresponding relationship. The in-tank pressure can ensure that the utilization rate of the working medium is the highest with the number of the target backflow paths whose backflow temperature reaches the preset temperature.

When a minimally invasive surgery of tumor is performed, the working medium used is generally divided into a cold working medium and a hot working medium. Correspondingly, the cold working medium is provided by a cold tank for storing the cold working medium, and the hot working medium is provided by a hot tank for storing the hot working medium. The cold tank and the hot tank will be described respectively below.

In an embodiment of the disclosure, the working medium storage tank includes a cold tank for storing the cold working medium. Correspondingly, step 104 may be specifically implemented through the following step. The number of target backflow paths whose backflow temperature is not higher than a first preset temperature is counted.

For the cold working medium, the preset temperature is a very low temperature. When counting is performed, the number of the target backflow paths whose backflow temperature is not higher than the first preset temperature is counted, and −190° C. may be selected as the first preset temperature.

In an embodiment of the disclosure, with respect to the cold working medium, the step 106 may specifically be implemented through the following steps. A target in-tank pressure corresponding to the number of the target backflow paths is determined according to the number of the target backflow paths and a corresponding relationship between a preset number of backflow paths and an in-tank pressure; and an adjustment instruction carrying the target in-tank pressure is sent to the cold tank, the adjustment instruction instructing the cold tank to open a pressurization valve or an air escape valve so as to adjust an in-tank pressure of the cold tank to the target in-tank pressure.

The cold tank is generally provided with a pressurization valve and an air escape valve. A coil pipe is provided close to a surface inside the cold tank. One end of the coil pipe is connected to the bottom of a liquid nitrogen tank, and the other end is connected at the pressurization valve. When the coil pipe performs heat exchanging with the outside, liquid nitrogen may be converted into nitrogen gas. When pressurization is required, the pressurization valve is opened, and the nitrogen gas may enter the inside of the cold tank, so as to realize the purpose of pressurization. When the air escape valve is opened, the cold tank may release the in-tank pressure, so as to realize the purpose of depressurization. Therefore, after the number of target backflow paths is counted, the target in-tank pressure corresponding to the number of the target backflow paths may be determined according to the number of the target backflow paths and the corresponding relationship between the preset number of backflow paths and the in-tank pressure. Then, the adjustment instruction carrying the target in-tank pressure is sent to the cold tank. After the cold tank receives the adjustment instruction, if it is identified that the pressurization is required, the pressurization valve is opened by activating the relay or by instruction control; and if it is identified that the depressurization is required, the air escape valve is opened by activating the relay or by instruction control.

In an embodiment of the disclosure, the valve box is also provided therein with a phase separation valve. Correspondingly, before step 102, the method may further include the following steps. An opened-closed state of each of cold valves is detected, the cold valve being a discharging valve of the cold working medium; the number of cold valves in an opened state is counted; if the number is not greater than a preset number, an opening instruction is sent to the valve box, the opening instruction instructing opening of the phase separation valve; and if the number is greater than the preset number, a closing instruction is sent to the valve box, the closing instruction instructing closing of the phase separation valve.

The phase separation valve has a function of quickly decreasing the temperature. In order to quickly decreasing the temperature of the ablation probe, the phase separation valve may be controlled to be opened when the number of opened cold valves is small. It is required to detect the opened-closed state of each of the cold valves, and the number of the cold valves in the opened state is counted. If the number is not greater than the preset number (in other words, the number of the opened cold valves is small), the opening instruction is sent to the valve box, so as to actuate the phase separation valve to open. It is certain that, if sufficient cold valves have been opened (that is, the number of the opened cold valves is greater than the preset number), it is indicated that the temperature may be decreased quickly. At this time, the closing instruction is sent to the valve box, so as to actuate the phase separation valve to close.

In an embodiment of the disclosure, a second thermocouple is provided at the phase separation valve. Correspondingly, after the step of sending the opening instruction to the valve box, the method may further include the following steps. A temperature at the phase separation valve collected by the second thermocouple is acquired; and if the temperature at the phase separation valve is not higher than a second preset temperature, a closing instruction is sent to the valve box.

Since the phase separation valve has a limited cold resistance capability, it is required to provide the second thermocouple at the phase separation valve (specifically at an outlet of the phase separation valve), so as to acquire the temperature at the phase separation valve collected by the second thermocouple in real time. If the temperature at the phase separation valve collected is not higher than the second preset temperature, it is indicated that the temperature at the phase separation valve is quite low enough, and it is required to send the closing instruction to the valve box, so as to actuate the phase separation valve to close, thereby preventing the phase separation valve from suffering from an overly low temperature.

Figure 6:
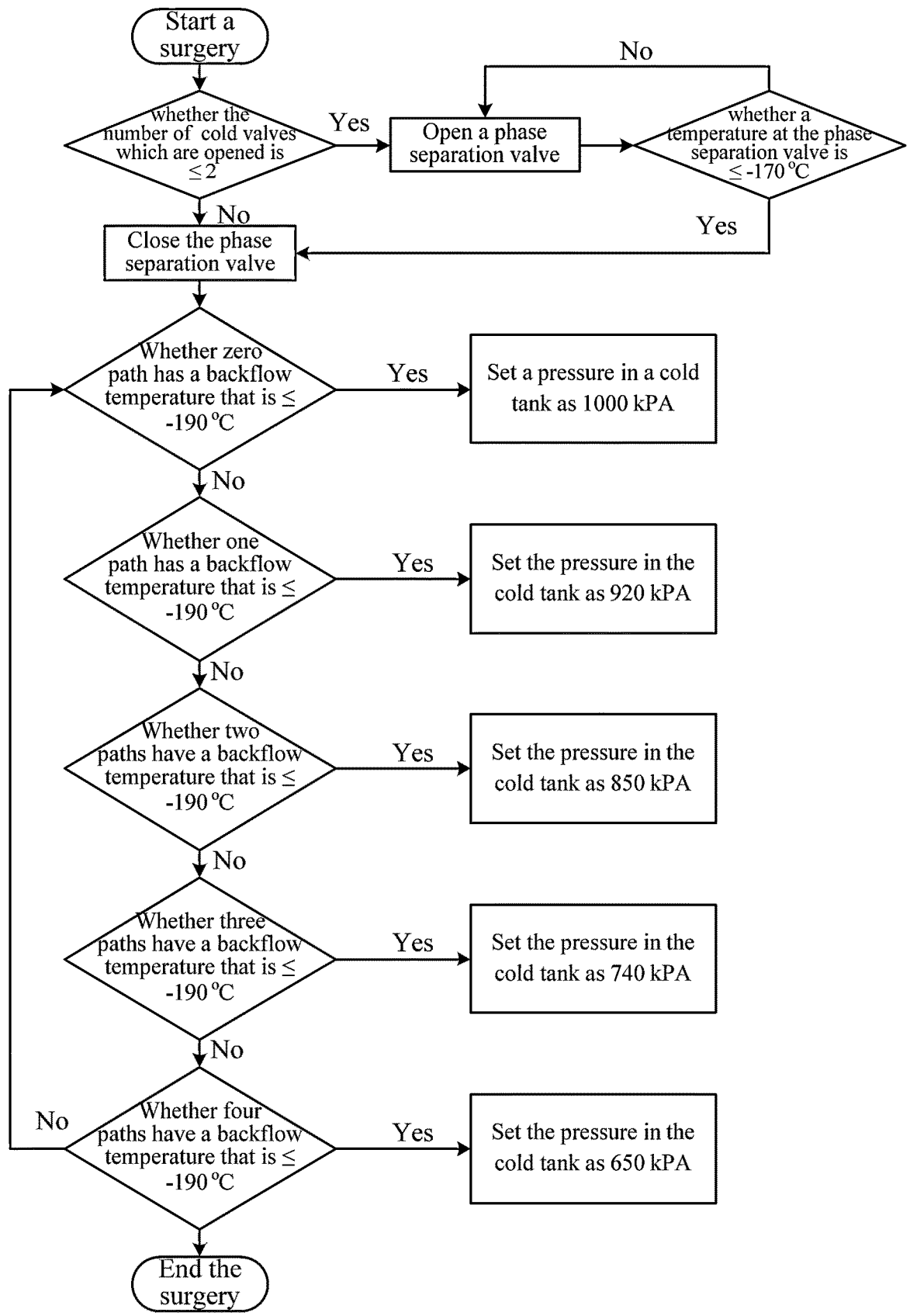
FIG. 6 schematically shows a flowchart of a process for adjusting an in-tank pressure of a cold tank provided according to an embodiment of the disclosure.

In specific implementation, the preset number in the above embodiment is generally set as 2, the second preset temperature at the phase separation valve is set as −170° C., and the first preset temperature is set as −190° C. A process of adjusting the in-tank pressure of the cold tank is as shown in FIG. 6. During the surgery, the number of cold valves which are opened is checked first, and it is determined whether the number of the cold valves which are opened is ≤2. If yes, it is required to open the phase separation valve, so as to improve a temperature decreasing rate; and if no, it is required to close the phase separation valve. Besides, it is required to acquire a temperature at the phase separation valve to determine whether the temperature at the phase separation valve is ≤−170° C. If yes, it is required to close the phase separation valve, so as to ensure that a consumption rate of the cold working medium (which is normally liquid nitrogen) is relatively low. In a treatment process, it is required to monitor backflow temperatures at the same time. Under a normal working state, the pressure in the cold tank is set as 1000 kPa. If it is monitored that one path has a backflow temperature that is ≤−190° C., it is required to decrease a pressure in the cold tank to 920 kPa. If it is monitored that two paths have a backflow temperature that is ≤−190° C., it is required to decrease the pressure in the cold tank to 850 kPa. If it is monitored that three paths have a backflow temperature that is ≤−190° C., it is required to decrease the pressure in the cold tank to 740 kPa. If it is monitored that four paths have a backflow temperature that is ≤−190° C., it is required to decrease the pressure in the cold tank to 650 kPa. It is known from actual testing that, in a simulative surgery experiment in which the system uses four probes at the same time for 20 minutes, a mode of using feedbacks of the backflow temperature to adjust the pressure in the cold tank can reduce the consumption of the cold working medium to 2/3 of the consumption before the adjustment.

In an embodiment of the disclosure, the working medium storage tank includes a hot tank for storing the hot working medium. Correspondingly, step 104 may be specifically implemented through the following step. The number of target backflow paths whose backflow temperature is not lower than a third preset temperature is counted.

For the hot working medium, the preset temperature is a relatively high temperature. When counting is performed, the number of the target backflow paths whose backflow temperature is not lower than the third preset temperature is counted, and 85° C. may be selected as the third preset temperature.

In an embodiment of the disclosure, with respect to the hot working medium, the step 106 may specifically be implemented through the following steps. A target in-tank pressure corresponding to the number of the target backflow paths is determined according to the number of the target backflow paths and a corresponding relationship between a preset number of backflow paths and an in-tank pressure; and an adjustment instruction carrying the target in-tank pressure is sent to the hot tank, the adjustment instruction instructing the hot tank to turn on a heater or open an air escape valve so as to adjust an in-tank pressure of the hot tank to the target in-tank pressure.

The hot tank is generally provided with a heater and an air escape valve. When the heater is turned on, the hot working medium in the hot tank is heated continuously, and the pressure in the hot tank increases. When the air escape valve is opened, the hot tank may release the in-tank pressure, so that the in-tank pressure of the hot tank is decreased. Therefore, after the number of target backflow paths is counted, the target in-tank pressure corresponding to the number of the target backflow paths may be determined according to the number of the target backflow paths and the corresponding relationship between the preset number of backflow paths and the in-tank pressure. Then, the adjustment instruction carrying the target in-tank pressure is sent to the hot tank. After the hot tank receives the adjustment instruction, if it is identified that the pressurization is required, the heater is turned on by instruction control; and if it is identified that the depressurization is required, the air escape valve is opened by activating the relay or by instruction control.

Figure 7:
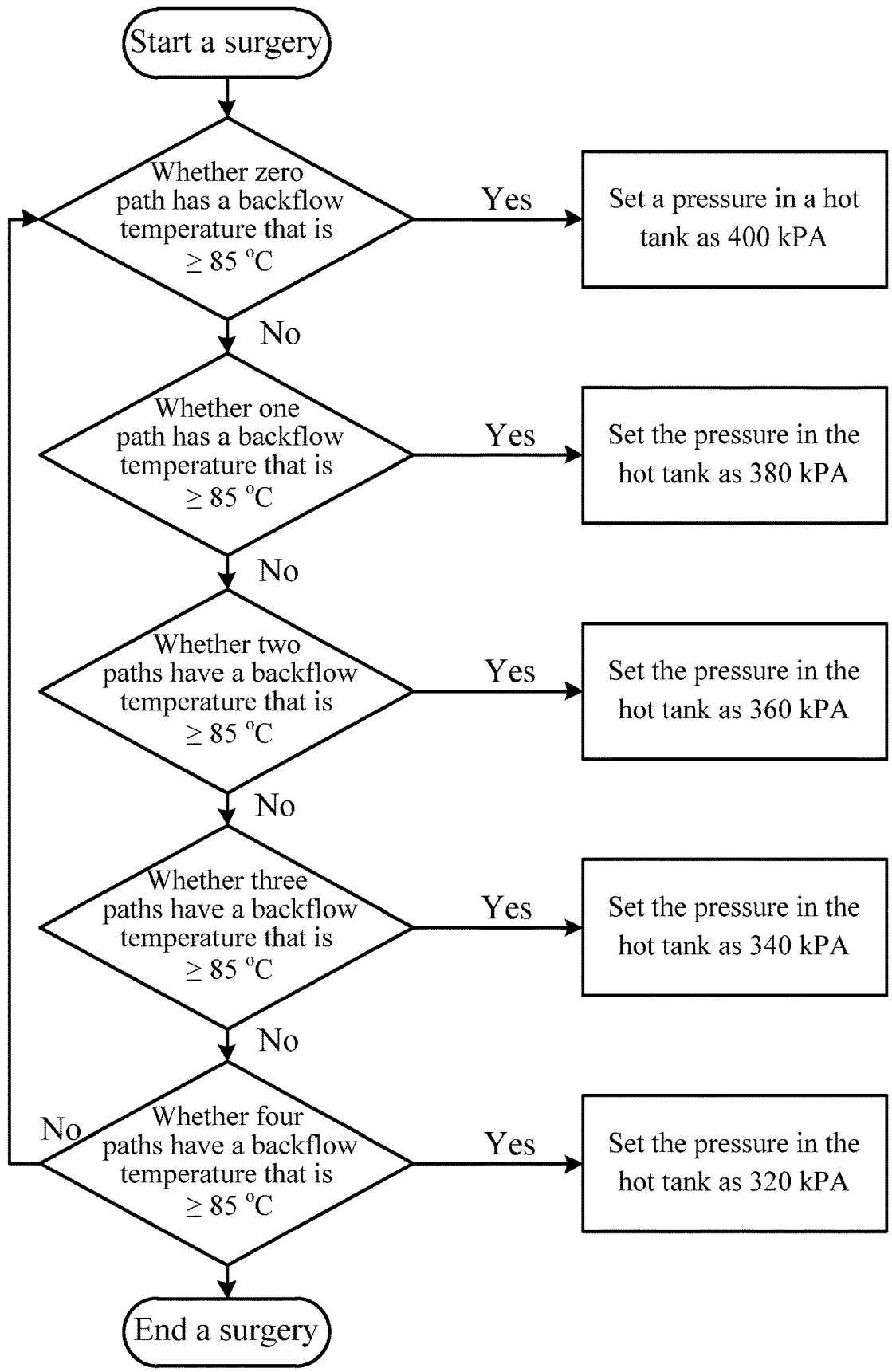
FIG. 7 schematically shows a flowchart of a process for adjusting an in-tank pressure of a hot tank provided according to an embodiment of the disclosure.

In specific implementation, the third preset temperature in the above embodiment is set as 85° C. A process of adjusting the in-tank pressure of the hot tank is as shown in FIG. 7. During the surgery, it is required to monitor backflow temperatures at the same time. Under a normal working state, a pressure in the hot tank is set as 400 kPa. If it is monitored that one path has a backflow temperature that is ≥85° C., it is required to decrease a pressure in the hot tank to 380 kPa. If it is monitored that two paths have a backflow temperature that is ≥85° C., it is required to decrease the pressure in the hot tank to 360 kPa. If it is monitored that three paths have a backflow temperature that is ≥85° C., it is required to decrease the pressure in the hot tank to 340 kPa. If it is monitored that four paths have a backflow temperature that is ≥85° C., it is required to decrease the pressure in the hot tank to 320 kPa.

According to the embodiment of the disclosure, the control box acquires the backflow temperature collected by each of the first thermocouples, counts the number of the target backflow paths whose backflow temperature reaches the preset temperature, and adjusts the in-tank pressure of the working medium storage tank to the target in-tank pressure corresponding to the number of the target backflow paths according to the number of the target backflow paths and the corresponding relationship between the preset number of the backflow paths and the in-tank pressure. The control box determines the target in-tank pressure corresponding to the number of the target backflow paths to realize automatic adjustment of the in-tank pressure of the working medium storage tank by acquiring the backflow temperature collected by each of the first thermocouples and counting the number of the target backflow paths whose backflow temperature reaches the preset temperature, and makes the flow of the working medium delivered change automatically accordingly to better adapt to an actual treatment scene and reduce the unnecessary waste of the working medium by automatically adjusting the in-tank pressure of the working medium storage tank.

Figure 8:
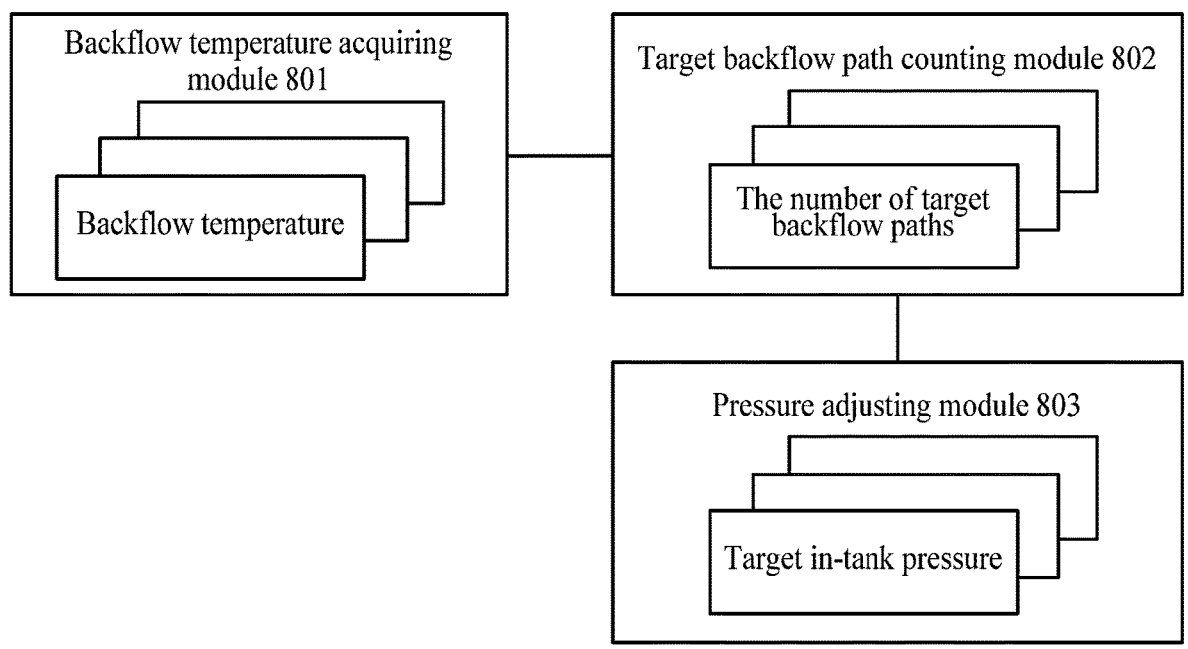
FIG. 8 schematically shows a structure of an apparatus for adjusting an in-tank pressure of a working medium storage tank provided according to an embodiment of the disclosure.

Corresponding to the above method embodiment, the disclosure further provides an embodiment of an apparatus for adjusting an in-tank pressure of a working medium storage tank. FIG. 8 shows a structure of an apparatus for adjusting an in-tank pressure of a working medium storage tank provided according to an embodiment of the disclosure.

As shown in FIG. 8, the apparatus for adjusting the in-tank pressure of the working medium storage tank includes:
- a backflow temperature acquiring module 801, which is configured to acquire a backflow temperature collected by each of first thermocouples;
- a target backflow path counting module 802, which is configured to count the number of target backflow paths whose backflow temperature reaches a preset temperature; and
- a pressure adjusting module 803, which is configured to adjust an in-tank pressure of the working medium storage tank to a target in-tank pressure corresponding to the number of the target backflow paths according to the number of the target backflow paths and a corresponding relationship between a preset number of backflow paths and the in-tank pressure.

Optionally, the target backflow path counting module 802 is specifically configured to: count the number of target backflow paths whose backflow temperature is not higher than a first preset temperature.

Optionally, the pressure adjusting module 803 may be specifically configured to: determine a target in-tank pressure corresponding to the number of the target backflow paths according to the number of the target backflow paths and a corresponding relationship between a preset number of backflow paths and an in-tank pressure; and send an adjustment instruction carrying the target in-tank pressure to the cold tank, the adjustment instruction instructing the cold tank to open a pressurization valve or an air escape valve so as to adjust the in-tank pressure of the cold tank to the target in-tank pressure.

Optionally, the apparatus may include:
- a detection module, which is configured to detect an opened-closed state of each of cold valves, the cold valve being a discharging valve of the cold working medium;
- a cold valve number counting module, which is configured to count the number of cold valves in an opened state; and
- an instruction sending module, which is configured to: send an opening instruction to a valve box if the number is not greater than a preset number, the opening instruction instructing opening of a phase separation valve; and send a closing instruction to the valve box if the number is greater than the preset number, the closing instruction instructing closing of the phase separation valve.

Optionally, the apparatus further includes:
- a phase separation valve temperature acquiring module, which is configured to acquire a temperature at the phase separation valve collected by a second thermocouple provided at the phase separation valve; and
- an instruction sending module, which is configured to send a closing instruction to the valve box if the temperature at the phase separation valve is not higher than a second preset temperature.

Optionally, a target backflow path counting module 802 may be specifically configured to: count the number of target backflow paths whose backflow temperature is not lower than a third preset temperature.

Optionally, a pressure adjusting module 803 may be specifically configured to: determine a target in-tank pressure corresponding to the number of the target backflow paths according to the number of the target backflow paths and a corresponding relationship between a preset number of backflow paths and an in-tank pressure; and send an adjustment instruction carrying the target in-tank pressure to the hot tank, the adjustment instruction instructing the hot tank to turn on a heater or open an air escape valve so as to adjust the in-tank pressure of the hot tank to the target in-tank pressure.

Optionally, the apparatus further includes:
- a backflow temperature sending module, which is configured to send the backflow temperature collected by each of the first thermocouples to an upper computer for display.

Optionally, the apparatus further includes:
- an ambient temperature acquiring module, which is configured to acquire an ambient temperature collected by a temperature sensor, the temperature sensor being provided on a temperature collecting circuit board which is provided in the control box, a fan and the heater being provided in the control box for adjusting the ambient temperature of the temperature collecting circuit board; and
- an actuating module, which is configured to: actuate the heater to work if the ambient temperature is lower than a fourth preset temperature; and actuate the fan to work if the ambient temperature is higher than a fifth preset temperature, the fifth preset temperature being higher than the fourth preset temperature.

Optionally, the heater is connected to a normally open contact of a first relay, and a positive temperature coefficient thermistor is connected in series in a coil loop of the first relay; and
- an actuating module is specifically configured to actuate the heater to work with the normally open contact of the first relay closed if the ambient temperature is lower than the fourth preset temperature, a resistance value of the positive temperature coefficient thermistor is decreased to a first preset resistance value, and a current passing through the coil loop of the first relay is increased to a first preset current value.

Optionally, the fan is connected to a normally open contact of a second relay, and a negative temperature coefficient thermistor is connected in series in a coil loop of the second relay; and
- an actuating module is specifically configured to actuate the fan to work with the normally open contact of the second relay closed if the ambient temperature is higher than the fifth preset temperature, a resistance value of the negative temperature coefficient thermistor is decreased to a second preset resistance value, and a current passing through the coil loop of the second relay is increased to a second preset current value.

According to the embodiment of the disclosure, the control box acquires the backflow temperature collected by each of the first thermocouples, counts the number of the target backflow paths whose backflow temperature reaches the preset temperature, and adjusts the in-tank pressure of the working medium storage tank to the target in-tank pressure corresponding to the number of the target backflow paths according to the number of the target backflow paths and the corresponding relationship between the preset number of the backflow paths and the in-tank pressure. The control box determines the target in-tank pressure corresponding to the number of the target backflow paths to realize automatic adjustment of the in-tank pressure of the working medium storage tank by acquiring the backflow temperature collected by each of the first thermocouples and counting the number of the target backflow paths whose backflow temperature reaches the preset temperature, and makes the flow of the working medium delivered change automatically accordingly to better adapt to an actual treatment scene and reduce the unnecessary waste of the working medium by automatically adjusting the in-tank pressure of the working medium storage tank.

The above content is an exemplary solution of the apparatus for adjusting the in-tank pressure of the working medium storage tank in the embodiment. It should be noted that, this technical solution of the apparatus for adjusting the in-tank pressure of the working medium storage tank and the above technical solution of the method for adjusting the in-tank pressure of the working medium storage tank belong to the same concept, and for details not explained in the technical solution of the apparatus for adjusting the in-tank pressure of the working medium storage tank, reference can be made to the above description of the technical solution of the method for adjusting the in-tank pressure of the working medium storage tank.

It should be noted that, respective components in the apparatus shall be understood as functional modules that must be established to implement steps of a program flow or steps of the method, and respective functional modules are not defined by actual functional divisions or separations. An apparatus defined by such a group of functional modules shall be understood as a functional module architecture that implements the solution mainly by using a computer program recited in the description, and shall not be understood as a physical device that implements the solution mainly by a hardware manner.

Figure 9:
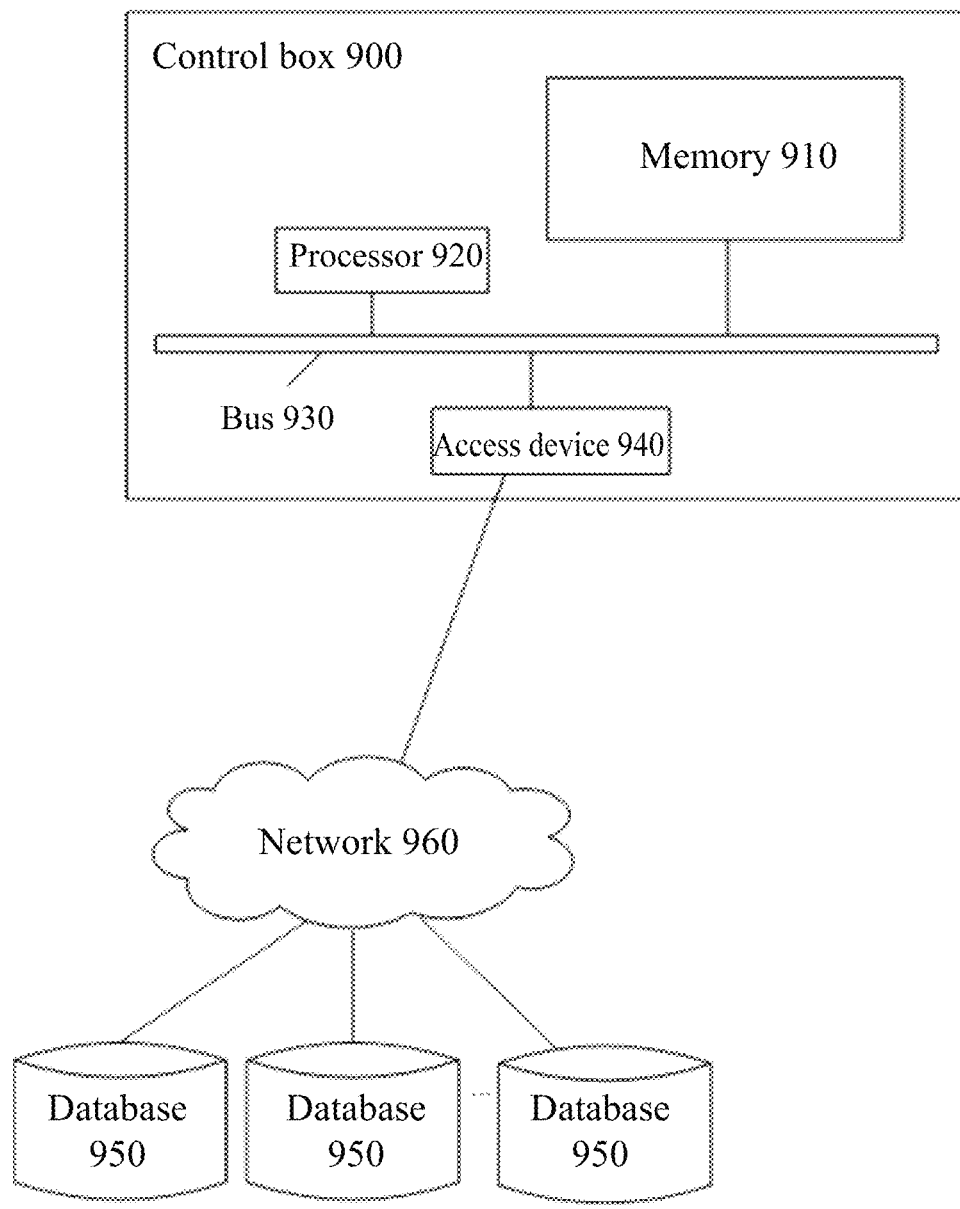
FIG. 9 schematically shows a structure of a control box provided according to an embodiment of the disclosure.

FIG. 9 shows a block diagram of a structure of a control box 900 provided according to an embodiment of the disclosure. Components of the control box 900 include, but are not limited to, a memory 910 and a processor 920. The processor 920 and the memory 910 are connected via a bus 930, and a database 950 is configured to save data.

The control box 900 further includes an access device 940, and the access device 940 enables the control box 900 to perform communication via one or more networks 960. Examples of these networks include a public switched telephone network (PSTN), a local area network (LAN), a wide area network (WAN), a personal area network (PAN), and a combination of communication networks such as the internet. The access device 940 may include one or more of any type of wired or wireless network interfaces (for example, a network interface card (NIC)), such as a wireless interface of the IEEE802.11 wireless local area networks (WLAN), an interface of the world interoperability for microwave access (Wi-MAX), an interface of the Ethernet, an interface of the universal serial bus (USB), an interface of the cellular network, an interface of the Bluetooth, an interface of the near field communication (NFC), and the like.

In an embodiment of the disclosure, the above components of the control box 900 and other components not shown in FIG. 9 are also connected to each other, for example, via the bus. It should be understood that the block diagram of the structure of the control box shown in FIG. 9 is only for the purpose of illustration only, rather than limiting the scope of the disclosure. Those skilled in the art may add or replace other components according to needs.

The control box 900 may be any type of stationary or movable computer devices, which include a movable computer or computing device (for example, a tablet computer, a personal digital assistant, a laptop computer, a notebook computer, a netbook, and the like), a mobile phone (for example, a smart phone), a wearable computing device (for example, a smart watch, smart glasses, and the like), or other types of movable devices, or a stationary computing device such as a desktop computer, or a PC. The control box 900 may also be a movable or stationary server.

The processor 920 is configured to execute the following computer executable instructions. When the processor 920 executes the computer executable instructions, steps of the method for adjusting the in-tank pressure of the working medium storage tank are implemented.

The above content is an exemplary solution of the control box in the embodiment. It should be noted that, this technical solution of the control box and the above technical solution of the method for adjusting the in-tank pressure of the working medium storage tank belong to the same concept, and for details not explained in the technical solution of the control box, reference can be made to the above description of the technical solution of the method for adjusting the in-tank pressure of the working medium storage tank. It is certain that, in another embodiment of the disclosure, the control box may implement the steps of the method for adjusting the in-tank pressure of the working medium storage tank by using a hardware circuit provided in the control box.

An embodiment of the disclosure further provides a computer readable storage medium, which stores a computer instruction. When the computer instruction is executed by a processor, the steps of the method for adjusting the in-tank pressure of the working medium storage tank described above are implemented.

The above content is an exemplary solution of the computer readable storage medium in the embodiment. It should be noted that, this technical solution of the storage medium and the above technical solution of the method for adjusting the in-tank pressure of the working medium storage tank belong to the same concept, and for details not explained in the technical solution of the storage medium, reference can be made to the above description of the technical solution of the method for adjusting the in-tank pressure of the working medium storage tank.

An embodiment of the disclosure discloses a chip, which stores a computer instruction. When the computer instruction is executed by a processor, the steps of the method for adjusting the in-tank pressure of the working medium storage tank described above are implemented.

The above content describes a specific embodiment of the disclosure. Other embodiments fall into the scope of the appended claims. In some cases, actions or steps recited in the claims may be performed according to an order different from the order described in the embodiment, but may still realize an expected result. In addition, it is not necessary to implement a process depicted in the drawings according to a specific order shown or a continuous order to realize the expected result. In some embodiments, multi-task processing and parallel processing may be possible or may be favorable.

The computer instruction includes a computer program code. The computer program code may be in a source code form, in an object code form, an executable file, or in some intermediate forms, and the like. The computer readable medium may include any entity or device that can carry the computer program code, a recording medium, a USB flash disk, a mobile hard disk drive, a magnetic disk, an optical disk, a computer memory, a read-only memory (ROM), a random access memory (RAM), an electrical carrier signal, a telecommunications signal, a software distribution package, and the like. It should be noted that, the content included in the computer readable medium may be added or reduced properly according requirements of legislative and patent practice in a judicial district. For example, in some judicial districts, according to the legislative and patent practice, the computer readable medium does not include the electrical carrier signal and the telecommunications signal.

Figure 10:
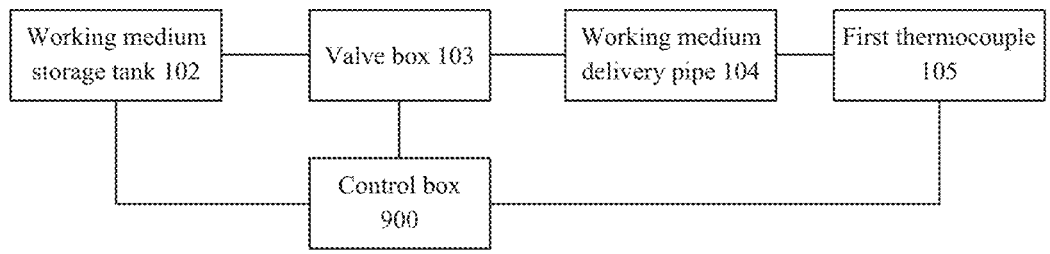
FIG. 10 schematically shows a structure of another combined cryoablation and hyperthermia system provided according to an embodiment of the disclosure.

The disclosure also provides a combined cryoablation and hyperthermia system. FIG. 10 shows a combined cryoablation and hyperthermia system provided according to an embodiment of the disclosure, which includes a control box 900, a working medium storage tank 102 for storing a working medium, a valve box 103 provided with multiple working medium discharging valves, a working medium delivery pipe 104 connected to an outlet of each of the multiple working medium discharging valves and for delivering the working medium to an ablation probe, and a first thermocouple 105 provided in each of working medium delivery pipes and for collecting a backflow temperature of each of paths. The control box 900 is the same as the control box shown in FIG. 9, and details are not repeated herein.

Figure 11:
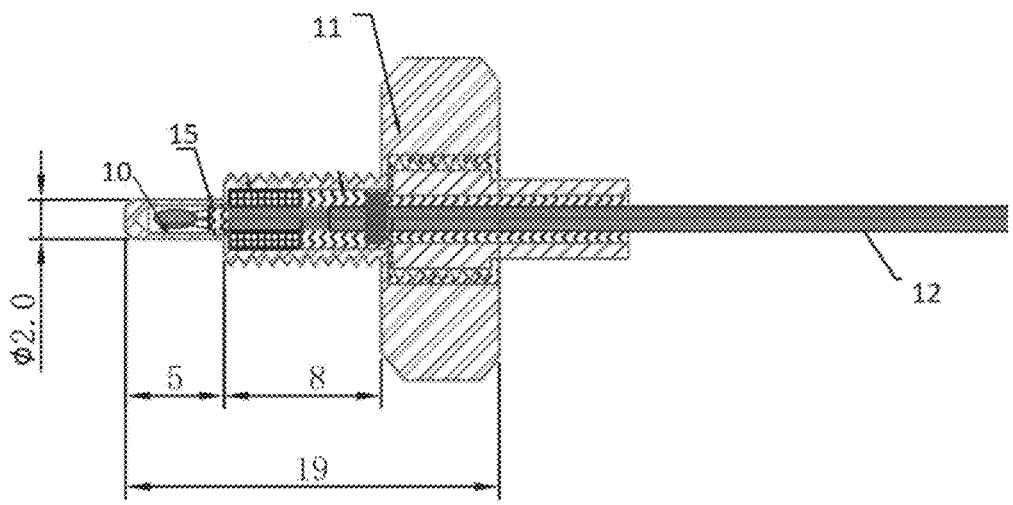
FIG. 11 schematically shows a structure of a thermocouple in existing technologies.

In existing technologies, a common structure of a thermocouple is as shown in FIG. 11. A sheathed thermocouple housing 15 of the thermocouple directly contacts a working medium, and then energy is conducted to a temperature probe 10 by heat conduction. However, there is an air clearance between the sheathed thermocouple housing 15 and the temperature probe 10, and the air is a poor conduction medium of heat. Therefore, there is a certain time delay for displaying a temperature. Moreover, the sheathed thermocouple housing 15 and a fixation base are connected by a metal, which may conduct the energy to the outside. Accordingly, the temperature displayed may be higher when cold energy is measured, and the temperature displayed may be lower when hot energy is measured.

In order to handle the above problem, in an embodiment of the disclosure, the first thermocouple includes a base and a temperature probe lead sealed in a hollow cavity of the base. A temperature measuring end of the temperature probe lead passes through the cavity in the base and exposes to the outside, and a distance from an end portion of the temperature measuring end to an end portion of an adjacent side of the base does not exceed 2 mm.

In an embodiment of the disclosure, the base includes a fixation base having a hollow cavity, and a tube fixed in the hollow cavity of the fixation base. A temperature probe lead is sealed in the tube, and a temperature measuring end passes through the tube and exposes to the outside, a distance from an end portion of the temperature measuring end to an end portion of the tube does not exceed 2 mm. According to the structure of this part, the longer the distance from the end portion of the temperature measuring end to the end portion of the tube is, the more sensitive a temperature probe is. However, since a wire of the thermocouple for measuring a temperature is soft, if the distance from the end portion of the temperature measuring end to the end portion of the tube exceeds 2 mm, there may be a risk that the temperature measuring end of the thermocouple is attached to a metal inner wall or is cut off. If the distance from the end portion of the temperature measuring end to the end portion of the tube is less than 1 mm, the sensitivity is slightly low. Therefore, it is preferable that the distance from the end portion of the temperature measuring end to the end portion of the tube does not exceed 2 mm.

In an embodiment of the disclosure, the end portion of the tube passes through the hollow cavity of the fixation base, and a distance from the end portion of the tube to an end portion of the fixation base is at least 3 mm.

In an embodiment of the disclosure, the temperature probe lead and the tube are sealed together by a cure adhesive, and the cure adhesive is obtained by mixing glue and a coagulator according to a preset ratio.

Figure 12A:
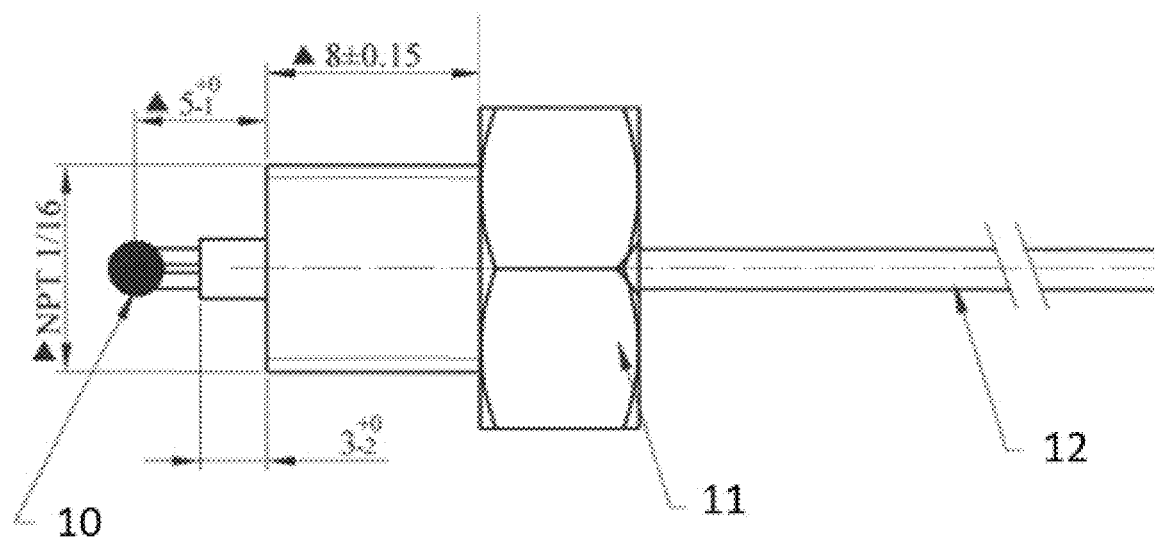
FIG. 12a schematically shows a structure of an improved thermocouple provided according to an embodiment of the disclosure.
Figure 12B:
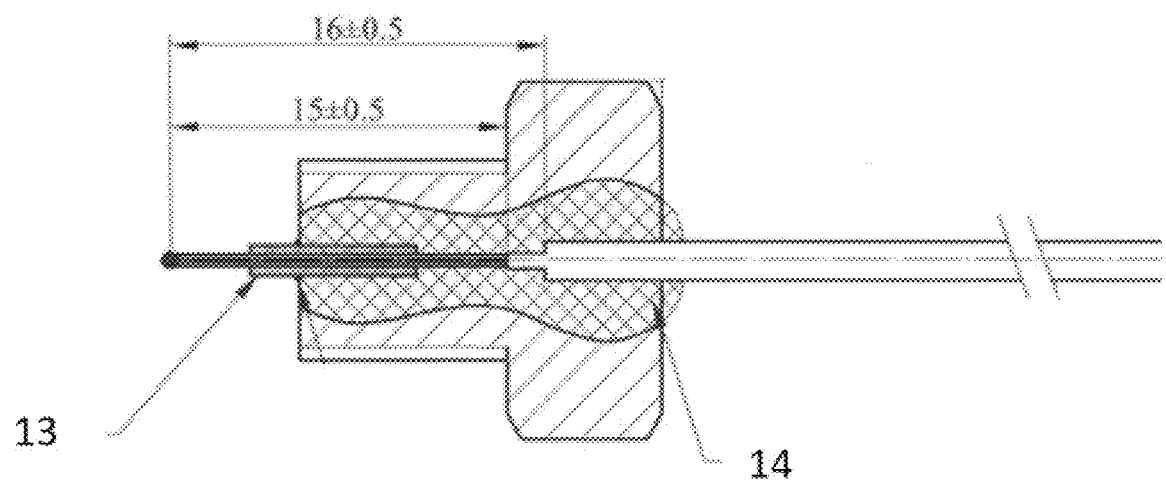
FIG. 12b schematically shows a sectional view of the improved thermocouple provided according to an embodiment of the disclosure.

In an embodiment of the disclosure, an improved structure of the thermocouple is as shown in FIG. 12a and FIG. 12b. This thermocouple does not include a sheath portion. An improvement is made to a portion of the temperature probe 10, and the temperature probe 10 directly exposes to the outside. In this way, the working medium may directly contact the temperature probe 10, and thus the circumstances of time delay and imprecise temperature measurement do not occur. However, in order to bear a working pressure of about 1000 kPa, it is required to redesign the portion of the temperature probe 10. A lead length (a length from a temperature measurement point to a fixation base 11) of the temperature probe 10 does not exceed 5 mm. That is, a distance from an end portion of the temperature measuring end to an end portion of an adjacent side of the base does not exceed 2 mm. A thermocouple wire 12 is fixed by a tube 13 (a copper tube is generally selected), and the copper tube goes beyond an end surface of the fixation base for at least 3 mm. A distance between the end portion of the temperature measuring end and an end portion of the tube 13 does not exceed 2 mm. The tube 13 and the fixation base 11 are welded by laser bonding and the like, and portions around the tube are welded well. At last, it is a cure adhesive 14 (which may be obtained by mixing glue and a coagulator according to a preset ratio). It should be noted that, if the ratio of the glue to the coagulator is less than 1:1.5, i.e., a circumstance that the glue is less, a sealing force of the glue is not sufficient, and leakage easily occurs at a sealed portion; and if the ratio of the glue to the coagulator is greater than 1:1.5, i.e., a circumstance that the glue is more, the glue may not cure for a long time or may cure at a surface but does not cure beneath the surface, so that a relatively large pressure cannot be born. Thus, it is preferable that the ratio of the glue to the coagulator is 1:1.5. The cure adhesive is filled into a clearance between tube 13 and the thermocouple wire 12. In particular, it is required to examine whether a portion where the temperature probe 10 extends out and a tail portion of the fixation base is fully filled. In an environment with a normal pressure and a normal temperature, the temperature probe is placed horizontally for 3 hours, and then is placed vertically for 24 hours. After that, an observation can be made whether the glue is cured. If the surface is smooth without a bubble and is not soft, it is indicated that the making of thermocouple is completed. Otherwise, it is required to perform processing again.

In general, the thermocouple in the embodiment of the disclosure has effects of sensitive temperature measurement feedback and temperature measurement without errors. The thermocouple mainly solves the problem that the thermocouple has an error of 3° C. to 5° C. (that is, when a measurement is performed on the liquid nitrogen with the temperature of −196° C., the temperature obtained is −193° C.) when being used to measure the temperature in a working environment (1000 kpa) with a relatively high pressure and a low temperature and the problem that the sensitivity of the temperature measurement feedback of the thermocouple is unsatisfactory (for example, when the measurement is performed on the liquid nitrogen with the temperature of −196° C., it takes 17 s to display a lowest temperature). In this way, a long-standing technical barrier on the problems in the industry is solved (in the industry, in order to know a treatment temperature of the ablation probe in real time, it is required to use one or several extra dedicated temperature measurement probes for piercing while a treatment probe is used, which adds unnecessary surgery operations). This plays a crucial role for the combined cryoablation and hyperthermia system to be used clinically, and can help the surgeon precisely and timely know the treatment temperature so as to ensure the surgery effect.

According to the embodiment of the disclosure, the combined cryoablation and hyperthermia system includes the control box, the working medium storage tank for storing the working medium, the valve box provided with multiple working medium discharging valves, the working medium delivery pipe connected to the outlet of each of the multiple working medium discharging valves and for delivering the working medium to the ablation probe, and the first thermocouple provided in each of the working medium delivery pipes and for collecting the backflow temperature of each of paths. The control box acquires the backflow temperature collected by each of the first thermocouples, counts the number of the target backflow paths whose backflow temperature reaches the preset temperature, and adjusts the in-tank pressure of the working medium storage tank to the target in-tank pressure corresponding to the number of the target backflow paths according to the number of the target backflow paths and the corresponding relationship between the preset number of the backflow paths and the in-tank pressure. The control box determines the target in-tank pressure corresponding to the number of the target backflow paths to realize automatic adjustment of the in-tank pressure of the working medium storage tank by acquiring the backflow temperature collected by each of the first thermocouples and counting the number of the target backflow paths whose backflow temperature reaches the preset temperature, and makes the flow of the working medium delivered changes automatically accordingly to better adapt to an actual treatment scene and reduce the unnecessary waste of the working medium by automatically adjusting the in-tank pressure of the working medium storage tank.

It should be noted that, for simplicity of description, the above method embodiments are described as a series of action combinations. However, it is known to those skilled in the art that, the disclosure is not limited by the order of the actions described, because some steps may be performed in another order or simultaneously. Moreover, it is also known to those skilled in the art that, the embodiments described in the description are all preferable embodiments, and the actions and modules involved are not indispensable.

In the above content, there is an emphasis in the description of each of the embodiments, and for details not explained in a certain embodiment, reference can be made to relevant description of other embodiments.

The above preferable embodiments of the disclosure disclosed are only used to explain the disclosure. The preferable embodiments do not describe all details, and do not limit this invention to the embodiments only. Obviously, various modifications and changes can be made based on the content of the disclosure. The disclosure selects and specifically describes these embodiments for better explaining principles and actual applications of the disclosure, so that those skilled in the art can better understand and utilize the disclosure. The disclosure is confined to the scope of claims and equivalents thereof.

The invention claimed is:

1. A method for adjusting an in-tank pressure of a working medium storage tank, the method comprising the steps of:
   providing a combined cryoablation and hyperthermia system, the combined cryoablation and hyperthermia system comprising:
   a control box,
   a plurality of working medium storage tanks, each being configured to store a working medium,
   a valve box provided with multiple working medium discharging valves,
   a plurality of working medium delivery pipes configured to deliver the working medium to an ablation probe, each being connected to an outlet of a respective one of the multiple working medium discharging valves, and
   a plurality of first thermocouples, each being provided in a respective one of the plurality of working medium delivery pipes and configured to collect a backflow temperature of a respective one of a plurality of paths
   acquiring the backflow temperature in each of the plurality of working medium delivery pipes collected by the plurality of first thermocouples;
   performing a determination of a magnitude of the backflow temperature to determine whether the backflow temperature reaches a preset temperature;
   counting a number of target backflow paths whose backflow temperature reaches the preset temperature; and
   adjusting an in-tank pressure of each of the plurality of working medium storage tanks to a target in-tank pressure corresponding to the number of the target backflow paths.

2. The method according to claim 1, wherein the plurality of working medium storage tanks comprises a cold tank for storing a cold working medium; and
   the step of counting the number of target backflow paths whose backflow temperature reaches the preset temperature comprises a step of:
   counting the number of target backflow paths whose backflow temperature is not higher than a first preset temperature.

3. The method according to claim 2, wherein the step of adjusting the in-tank pressure of each of the plurality of working medium storage tanks to the target in-tank pressure corresponding to the number of the target backflow paths comprises steps of:
   determining a target in-tank pressure corresponding to the number of the target backflow paths; and
   sending an adjustment instruction carrying the target in-tank pressure to the cold tank, wherein the adjustment instruction instructs the cold tank to open a pressurization valve or an air escape valve so as to adjust the in-tank pressure of the cold tank to the target in-tank pressure.

4. The method according to claim 2, wherein a phase separation valve is further provided in the valve box; each of the multiple working medium discharging valves comprising cold valves and
   before the step of acquiring the backflow temperature in each of the plurality of working medium delivery pipes, the method further comprises steps of:
   detecting an opened-closed state of each of the cold valves, wherein the cold valve is a discharging valve of the cold working medium;
   counting a number of the cold valves in an opened state;
   sending an opening instruction to the valve box if the number is not greater than a preset number, wherein the opening instruction instructs opening of the phase separation valve; and
   sending a closing instruction to the valve box if the number is greater than the preset number, wherein the closing instruction instructs closing of the phase separation valve.

5. The method according to claim 4, wherein a second thermocouple is provided at the phase separation valve; and after the step of sending the opening instruction to the valve box, the method further comprises steps of:
acquiring a temperature at an outlet of the phase separation valve; and
sending a closing instruction to the valve box if the temperature at the phase separation valve is not higher than a second preset temperature.

6. The method according to claim 1, wherein the plurality of working medium storage tanks comprises a hot tank for storing a hot working medium; and
the step of counting the number of target backflow paths whose backflow temperature reaches the preset temperature comprises a step of:
counting the number of target backflow paths whose backflow temperature is not lower than a third preset temperature.

7. The method according to claim 6, wherein the step of adjusting the in-tank pressure of each of the plurality of working medium storage tanks to the target in-tank pressure corresponding to the number of the target backflow paths comprises steps of:
determining a target in-tank pressure corresponding to the number of the target backflow paths; and
sending an adjustment instruction carrying the target in-tank pressure to the hot tank, wherein the adjustment instruction instructs the hot tank to turn on a heater or open an air escape valve so as to adjust the in-tank pressure of the hot tank to the target in-tank pressure.

8. The method according to claim 1, wherein the control box is provided therein with a temperature collecting circuit board and with a fan and a heater for adjusting an ambient temperature of the temperature collecting circuit board; and a temperature sensor is provided on the temperature collecting circuit board; and
the method further comprises steps of:
acquiring an ambient temperature collected by the temperature sensor;
actuating the heater to work if the ambient temperature is lower than a fourth preset temperature; and
actuating the fan to work if the ambient temperature is higher than a fifth preset temperature, wherein the fifth preset temperature is higher than the fourth preset temperature.

9. The method according to claim 8, wherein the heater is connected to a normally open contact of a first relay, and a positive temperature coefficient thermistor is connected in series in a coil loop of the first relay; and
the step of actuating the heater to work if the ambient temperature is lower than the fourth preset temperature comprises a step of:
actuating the heater to work with the normally open contact of the first relay closed, if the ambient temperature is lower than the fourth preset temperature, a resistance value of the positive temperature coefficient thermistor is decreased to a first preset resistance value, and a current passing through the coil loop of the first relay is increased to a first preset current value.

10. The method according to claim 8, wherein the fan is connected to a normally open contact of a second relay, and a negative temperature coefficient thermistor is connected in series in a coil loop of the second relay; and
the step of actuating the fan to work if the ambient temperature is higher than the fifth preset temperature comprises a step of:
actuating the fan to work with the normally open contact of the second relay closed, if the ambient temperature is higher than the fifth preset temperature, a resistance value of the negative temperature coefficient thermistor is decreased to a second preset resistance value, and a current passing through the coil loop of the second relay is increased to a second preset current value.

11. A control box, comprising: a memory and a processor; and
the memory is configured to store a computer executable instruction, and the processor is configured to execute the computer executable instruction, so as to implement steps of:
acquiring a backflow temperature in each of a plurality of working medium delivery pipes collected by a plurality of first thermocouples provided respectively in the plurality of working medium delivery pipes;
counting a number of target backflow paths whose backflow temperature reaches a preset temperature; and
adjusting an in-tank pressure of a working medium storage tank to a target in-tank pressure corresponding to the number of the target backflow paths.

12. A combined cryoablation and hyperthermia system, comprising the control box according to claim 11, a plurality of working medium storage tanks, each being configured to store a working medium, a valve box provided with multiple working medium discharging valves, a plurality of working medium delivery pipes configured to deliver the working medium to an ablation probe, each being connected to an outlet of a respective one of the multiple working medium discharging valves, and a plurality of first thermocouples, each being provided in a respective one of the plurality of working medium delivery pipes and configured to collect a backflow temperature of a respective one of a plurality of paths.

* * * * *